United States Patent [19]
Hsieh et al.

[11] Patent Number: 5,242,926
[45] Date of Patent: Sep. 7, 1993

[54] THERAPEUTIC COMPOSITION FOR TREATING HYPERTHYROIDISM

[75] Inventors: Ming T. Hsieh; Long Y. Wu, both of Taipei, Taiwan

[73] Assignee: National Science Council of Republic of China, Taipei, Taiwan

[21] Appl. No.: 889,414

[22] Filed: May 28, 1992

[51] Int. Cl.$^5$ .............................................. A61K 31/44
[52] U.S. Cl. .................................................... 514/284
[58] Field of Search ........................... 514/284; 546/71

[56] References Cited

U.S. PATENT DOCUMENTS 3,933,826  1/1976  Kametani ............................. 546/71
4,761,417  8/1988  Maroko ................................ 514/284

Primary Examiner—Frederick E. Waddell
Assistant Examiner—K. Weddington
Attorney, Agent, or Firm—Jacobson, Price, Holman & Stern

[57] ABSTRACT

The composition includes dl-tetrahydropalmatine mixed with its carrier having pharmaceutical therapeutical effect for treating hyperthyroidism. The dl-tetrahydropalmatine may be purified from a chloroform layer extracted from a Corydalis tuber.

3 Claims, No Drawings

THERAPEUTIC COMPOSITION FOR TREATING HYPERTHYROIDISM

BACKGROUND OF THE INVENTION

The thyroid is a major endocrine gland for maintaining a human metabolism equilibrium. Phenomena such as nervous tension, dietary imbalance, environmental pollution, misuse of drugs and disease infection may cause abnormal function of the thyroid. The current methods for treating thyroid symptoms include: surgery, radiation with radioactive isotopes and treatment with thyroid inhibitors.

There are two mechanisms of conventional antithyroxin medicines, one being a peroxidase for inhibiting iodide for reducing the synthesis of thyroxin; and the other for interfering the catching of iodide ions or inhibiting a combination of iodide ions with thyroid globulin, thereby reducing the concentration of thyroxin in the blood. However, conventional medicines may stimulate the thyrotropine-stimulating hormone (TSH) to enlarge thyroid cells to decrease the white blood cells and may inhibit the thyroid hormone especially in a pregnant mother, thereby influencing the brain growth of a baby and causing stunting and cretinism or even leading a worse side effect such as a deformed baby.

In view of these considerations, we therefore invent a therapeutic composition for treating hyperthyroidism but without causing side effects to the user.

SUMMARY OF THE INVENTION

The object of the present invention is to provide a Corydalis effective constituent of dl-tetrahydropalmatine extracted in a chloroform B layer for treating hyperthyroidism effectively.

DETAILED DESCRIPTION

The process for preparing the Corydalis composition and the experiments showing its effects are described in detail hereinafter.

Preparation of Therapeutic Composition and Test animals

Preparation of Corydalis extracts

One kg of the coarsely ground Corydalis Tuber is placed in a 10 l round flask with 1500 ml methanol. Hot dipping and extraction is performed 4 times in succession keeping a water bath temperature of 40° C. The extracted liquid is collected, filtered, mixed, concentrated and dried at reduced pressure to obtain the extract product (I) of the methanol layer.

A chloroform A layer (II), Chloroform B layer (III), n-butanol layer (IV) and water layer (V) may be respectively obtained by distribution and separation according to the flow chart below.

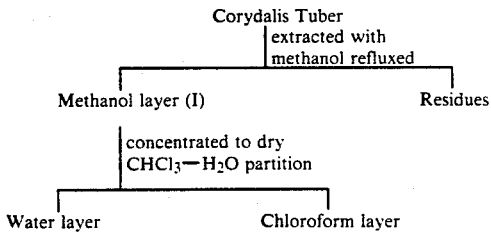
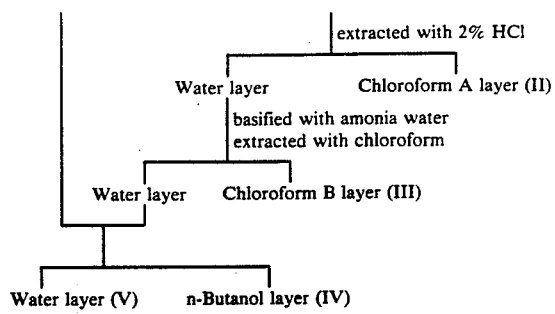

Separation of Corydalis Tuber

The above-separated chloroform B layer is fractionated by silica gel column, eluted with solvents and isolated by thin-layer chromatography to obtain protoberberine type alkaloids (PBT), which separately produce five pure substances CB-1-CB-5. A microhot-stage apparatus used for measuring the melting point of the products. Optical rotation is measured on a JASCO DIP-4 automatic polarimeter at room temperature as soluble in $CHCl_3$. NMR spectra are run on a Bruker Ac-250 spectrometer with tetramethylsilane as an internal standard. MS spectra are measured on a JEOL JMX-300 mass spectrometer at 70 eV.

The five protoberberine type alkaloids (PBT) thus obtained are identified with the above-mentioned spectral analysis as compared with standard control test to be the compounds as follows:

Chloroform B layer 1 (C-B1) dl-tetrahydrocoptisine: colorless needle like product ($CHCl_3$-MeOH), mp 199°–200.5° C.
$[\alpha]_D^{28} = -297.14°$ (c=0.119, $CHCl_3$).
$^1$H-NMR ($CDCl_3$) δ: 5.91 (2H, s, —O—$CH_2$—O—), 5.94 (2H, s, —O, $CH_2$—O—), 6.58 (1H, s, H-4), 6.63 (1H, d, J=8.05 Hz, H-12), 6.69 (1H, d, J=8.05 Hz, H-11), 6.69 (1H, d, J=8.05 Hz, H-11), 6.72 (1H, s, H-1).
MS (m/z, %): 323 (M+, 30), 174 (18), 148 (100).

Chloroform B layer 2 (C-B2) d-corydaline: colorless prism (MeOH-ether), mp 138°–139.5° C.
$[\alpha]_D^{26} = +317.29°$ (c=0.204, $CHCl_3$).
$^1$H-NMR ($CDCl_3$) δ: 0.95 (3H, d, J=6.84 Hz), 3.87 (12H, s, —$OCH_3X_4$), 6.61 (1H, s H-4), 6.69 (1H, s, H-1), 6.85 (1H, d, J=8.40 Hz, H-12), 6.91 (1H, d, J=8.40 Hz, H-11).
MS (m/z, %): 369 (M+, 60), 354 (19), 192 (10)., 190 (13), 178 (100), 163 (18).

Chloroform B layer 3 (C-B3) dl-tetrahydropalmatine: colorless needle like ($CHCl_3$-MeOH), mp 146°–147° C.
$[\alpha]_D^{28} = 0.0°$ (c=0.175, $CHCl_3$).
$^1$H-NMR ($CDCl_3$) δ: 3.85 (6H, s, —$OCH_3X_2$), 3.88 (6H, s, —$OCHX_2$), 6.62 (1H, s, H-4), 6.73 (1H, s, H-1), 6.79 (1H, d, J=8.34 Hz, H-12), 6.89 (1H, d, J=8.34 Hz, H-11).
MS (m/z, %): 355 (M+, 100), 354 (70), 190 (33), 164 (100), 149 (75).

Chloroform B layer 4 (C-B4) (-)-tetrahydrojatrorrhizine:
colorless/shapeless powder, mp 227°–229° C. (dec.).
$[\alpha]_D^{25} = -295.34°$ (c=0.175, $CHCl_3$).
$^1$H-NMR ($CDCl_3$) δ: 3.85 (6H, s, —$OCH_3X_2$), 3.87 (3H, s, —$OCH_3$), 6.58 (1H, s, H-4), 6.78 (1H, d, J=8.25

Hz, H-12), 6.81 (1H, s, H-1), 6.87 (1H, d, J=8.25 Hz, H-11).

MS (m/z, %): 341 (M+, 83), 340 (48), 310 (15), 164 (100), 149 (70).

Chloroform B layer 5 (C-B5) (±)-palmatine: yellow needle like (CHCl$_3$-MeOH), mp 234°-236° C. $[\alpha]_D^{28}=0°$ (c=0.164, CHCl$_3$).

$^1$H-NMR (CDCl$_3$) δ: 3.20 (2H, t, J=5.48 Hz, H-5), 3.96, 4.02, 4.08, 4.12 (each 3H, s, —OCH$_3$X$_4$), 5.13 (2H, t, J=5.48 Hz, H-6), 6.92 (1H, s, H-4), 7.15 (1H, s, H-1), 7.26 (1H, s, H-13), 7.88 (1H, d, J=9.33 Hz, H-12l), 7.94 (1H, d, J=9.33 Hz, H-11), 10.48 (1H, s, H-8).

MS (m/z, %): 352 (M+, 34), 351 (21), 149 (21), 148 (100).

The structural formula of dl-tetrahydropalmatine of this invention is identified as follows:

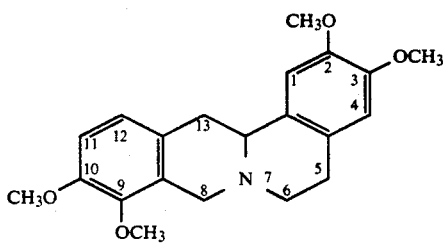

In accordance with the present invention, the Corydalis chloroform B layer, methanol layer, water layer and n-butanol layer are preliminarily tested to determine the effects of each on the hyperthyroidism of L-T4 induced female rats and on the thyroid function of normal rats.

Then, the purified most effective CB-3 dl-tetrahydropalmatine obtained from extracted product of chloroform B layer is tested for its effect on changes in thyroid function and its effect on the thyrotropine stimulating hormone (TSH) in blood and on the concentration of cholesterol and triglyceride of normal pregnant rats and L-T4 induced pregnant rats subjected to hyperthyroidism.

The following examples will show in detail the experiments and their results in relation, but not limited, to this invention in these examples:

EXPERIMENTAL ANIMALS

ICR mice may be used as testing animals in this invention, each having a weight of 18-25 grams. Sprague-Dawley rats each having a weight of 240±10 grams may also be used in this invention.

The mice or rats are placed in a metal cage by feeding 5 mice per group in each cage with solid foods and distilled water at least 1 week before performing the experiment at 22°±10° C. and humidity of 55±5%.

EXPERIMENT 1

Effect of each extracted layer of Corydalis on rat thyroid

The female Sprague-Dawley rats are respectively treated with Corydalis methanol layer, n-butanol layer, water layer and chloroform B layer for 50 mg/kg daily for a continuous dose per os for 14 days. On the 15th day, each rat is intraperitoneally injected with pentobarbital 50 mg/kg and narcotized. The rat abdominal cavity is cut to take the thyroid out for weighing and for examining pathological section, which is stained with H-E stain to facilitate observation of pathologic changes.

By repeating the above-mentioned procedures, a control test is performed by oral dose of PTU (propylthiouracil) 50 mg/kg.

Results

As shown in table 1, the normal rats, after being treated with Corydalis methanol layer, n-butanol layer, water layer and chloroform B layer 50 mg/kg daily for consecutive 14 days, show no statistically meaning for changes in thyroid in comparison with the control test. However, the group treated by PTU clearly shows an increase thyroid weight (P<0.001).

By observing the pathologic section of the thyroid, the normal rats after being treated with Corydalis layers show no noticeable effect on the thyroid cells. However, the rats treated with PTU show remarkable expansion of the thyroid follicle cells and their colloidal loss.

Observing

Therefore, the Corydalis extraction layers will not influence the thyroid weight, but the conventional antithyroid medicine PTU may increase thyroid weight. Meanwhile, the Corydalis layer will not form thyroid follicle cells. whereas the PTU will cause the formation of follicle cells, and loss of colloid.

TABLE 1

| Treatment | Weight (g) | Thyroid (mg/ 100 g weight) |
|---|---|---|
| Control group | 246 ± 14 | 8.9 ± 1.0 |
| Methanol layer (50 mg/kg) | 272 ± 9 | 8.4 ± 1.5 |
| n-butanol layer (50 mg/kg) | 261 ± 15 | 8.4 ± 1.0 |
| water layer (50 mg/kg) | 257 ± 15 | 7.6 ± 0.4 |
| Chloroform B layer (50 mg/kg) | 264 ± 6 | 8.4 ± 1.3 |
| PTU (50 mg/kg) | 261 ± 10 | 26.8 ± 2.5*** |

Mean ± SE (n = 6). PTU: propylthiouracil (***P < 0.001) Significantly different from control group.

EXPERIMENT 2

Effect of each Corydalis extracted layer on hyperthyroidism in rats.

Normal Group

The female Sprague-Dawley rats are continuously fed orally (P.O.) with Corydalis extracted methanol layer, n-butanol layer, water layer and chloroform B layer for a daily dose of 50 mg/kg for 14 days. On the 15th day, a 50 mg/kg pentobarbital is intraperitoneally injected into the rats which are narcotized. Then, the rat abdominal cavity is cut for extracting arterial blood, which blood is settled for 2 hours at room temperature and is centrifuged to separate the serum at 2500 rpm for 10 minutes. The concentrations of TSH, T3 (triiodothyroxine), T4 (thyroxin), free T3 and free T4 in the serum is measured by RIA analysis methods.

L-T4 induced Hyperthyroidism Group

The female Sprague-Dawley rats each having a weight of 250±10 grams are subcutaneously injected (S.C.) for 12 days with a daily dose of 300 μg/kg for each rat to induce hyperthyroidism. Then, the rats are treated per os with Corydalis extracted methanol layer, n-butanol layer, water layer and chloroform B layer, each for a daily dose of 50 mg/kg pentobarbital is intraperitoneally injected (I.P.) into each rat and the rat is narcotized. Then, the rat abdominal cavity is cut to extract arterial blood which is settled for 2 hours at room temperature and is centrifuged at 2500 rpm for 10 minutes for separating the serum.

The concentrations of TSH, T3, T4, free T3 and free T4 in the serum by RIA methods. The normal control group is treated PTU 5 mg/kg (P.O.) in similar procedures as described above.

Result:

(1) As shown in Table 2, after treating the Corydalis extracted methanol layer, n-butanol layer, water layer and chloroform B layer each for 50 mg/kg for continuous 14 days, the Corydalis extracted methanol layer may remarkably reduce the FT4 concentration in the normal rat serum (P<0.05); water layer may also reduce FT4 in rat blood (P<0.05); and the chloroform B layer may remarkably reduce FT3 (P<0.05) and FT4 (P<0.05) in the normal rat blood; and the n-butanol layer shows no effect on the FT4, FT3 concentration.

TABLE 2

| Treatment | TSH (μu/ml) | T3 (ng/dl) | T4 (μg/dl) | FT3 (ng/dl) | FT4 (ng/dl) |
| --- | --- | --- | --- | --- | --- |
| Normal (Control) group | 2.63 ± 0.38 | 39.77 ± 6.01 | 2.21 ± 0.21 | 1.15 ± 0.09 | 1.94 ± 0.29 |
| Methanol layer | 2.60 ± 0.46 | 38.2 ± 3.16 | 1.88 ± 0.37 | 0.85 ± 0.25 | 1.36 ± 0.21* |
| n-butanol layer | 2.63 ± 0.34 | 43.35 ± 3.76 | 2.34 ± 0.4 | 0.98 ± 0.33 | 1.72 ± 0.27 |
| Water layer | 2.81 ± 0.41 | 43.27 ± 8.25 | 2.1 ± 0.24 | 1.02 ± 0.24 | 1.34 ± 0.32* |
| Chloroform B layer | 2.19 ± 0.34 | 38.18 ± 4.36 | 1.98 ± 0.28 | 0.80 ± 0.17* | 1.29 ± 0.29* |

Mean ± SE (n = 6)
Significantly different from normal group (*P < 0.05)

(2) As shown in Table 3, the Corydalis extracted methanol layer (50 mg/kg) may remarkably reduce T3 (P<0.05), T4 (P<0.05), FT3 (P<0.01) and FT4 (P<0.01) in the blood of hyperthyroidism rats induced with L-T4, and shows no influence on the TSH; n-butanol layer (50 mg/kg) remarkably decreases T3 (P<0.05), T4 (P<0.05), FT3 (P<0.001) and FT4 (P<0.05) in blood and shows no effect on TSH; water layer (50 mg/kg) remarkably decreases T3 (P<0.01), T4 (P< 0.05), FT3 (P<0.01) and FT4 (P<0.05) in rat blood and shows no significant difference on TSH; and the chloroform B layer (50 mg/kg) shows a most remarkable reduction of T3 (P<0.01), T4 (P<0.001), FT3 (P<0.001) and FT4 (P<0.01) in blood and shows no statistical difference on TSH value.

As to the PTU (5 mg/kg), it may remarkably reduce the concentrations of T3 (P <0.001), T4 (P<0.001), FT3 (P<0.01) and FT4 (P<0.001), but remarkably increase TSH (P<0.01). This shows that PTU & Corydalis produce their effects by obviously different mechanisms.

Corydalis.

TABLE 3

| Treatment | TSH (μg/ml) | T3 (ng/dl) | T4 (μg/dl) | FT3 (ng/dl) | FT4 (ng/dl) |
| --- | --- | --- | --- | --- | --- |
| Hyperthyroidism group (HP) | 1.01 ± 0.10 | 63.94 ± 14.28 | 4.68 ± 0.78 | 4.15 ± 0.10 | 6.42 ± 1.42 |
| HP + methanol layer 50 mg/kg | 1.03 ± 0.07 | 39.92 ± 4.74* | 2.85 ± 0.35* | 2.48 ± 0.38* | 2.88 ± 0.48** |
| HP + n-butanol layer 50 mg/kg | 1.12 ± 0.10 | 34.02 ± 9.64* | 2.87 ± 0.68* | 2.47 ± 0.26** | 3.68 ± 0.90* |
| HP + water layer 50 mg/kg | 1.2 ± 0.19 | 28.78 ± 4.96** | 2.97 ± 0.78* | 2.44 ± 0.36** | 3.87 ± 0.89* |
| HP + chloroform B layer 50 mg/kg | 1.08 ± 0.28 | 26.91 ± 1.43*** | 2.57 ± 0.49** | 1.80 ± 0.37*** | 2.58 ± 0.46** |
| HP + PTU 5 mg/kg | 3.98 ± 0.40** | 17.92 ± 1.43*** | 1.11 ± 0.02*** | 0.44 ± 0.02*** | 0.47 ± 0.04 |

Mean ± SE (n = 6)
HP: Hyperthyroidism induced by L-T4 300 μg/kg for 12 days.
Significantly different from HP (*P < 0.05; P < 0.01; *P < 0.001)

Observing:

According to these experiments, it is known that the Corydalis extracted chloroform B layer will most remarkably decrease the T3, T4, FT3 and FT4 in the bloods of hyperthyroidism rats.

It is therefore expected to further separate the chloroform B layer extracted from Corydalis tuber to obtain PBT and purified product, di-tetrahydropalmatine (THP), which is further tested to show its effects on thyroid function, TSH concentration changes, cholesterol and triglyceride in rats.

EXPERIMENT 3

Effect of PBT and THP on rats (1) Normal group:

The female Sprague-Dawley rats, each weights 270±15 grams, are divided into 5 groups of 6 rats, for following daily treatment for continuous 10 days, except a normal group for control. A first and second group respectively treated with PBT 25 mg/kg and 50 mg/kg (P.O.); a third group treated with THP 5 mg/kg (I.P.); and a fourth group treated with PTU 5 mg/kg (P.O.).

On the eleventh days, each rat is injected (I.P.) with pentobarbital 50 mg/kg and narcotized for extracting arterial blood which is settled for 2 hours at room temperature and centrifuged at 2500 rpm for 10 minutes to separate the serum. The concentrations of TSH, T3, T4, FT3 and FT4 in bloods are analyzed by RIA methods. The normal control group is treated with saline and analyzed by the same methods.

(2) L-T4 induced hyperthyroidism group:

The female Sprague-Dawley rats, each weighs 260±15 grams, are divided into 5 groups of 6 rats, each rat being subcutaneously injected (s.c.) with L-T4 300 µg/kg daily for continuous 12 days to induce hyperthyroidism in each rats. Two groups are respectively treated with daily PBT 25 mg/kg and 50 mg/kg (P.O.); one group is treated with daily THP 5 mg/kg (I.P.) and the other group treated with daily PTU 5 mg/kg (P.O.). The control group is treted with saline. After continuous treatment of 10 days as described above, each rat is injected (I.P.) with pentobarbitol 50 mg/kg and narcotized on the eleventh day, and then extracted the arterial blood for measuring concentrations of TSH, T3, T4, FT3 and FT4 in the bloods.

Results:

(1) As shown in Table 4, the normal rats after being treated with PBT (25 mg/kg). PBT (50 mg/kg, I.P.) show no significnt statistical difference from the control test for the concentrations of TSH, T3, T4, FT3 and FT4 in the rat bloods; and the rats treated with PTU (5 mg/kg, P.O.) will remarkably reduce T3 ($P<0.001$), T4 ($P<0.001$), FT3 ($P<0.001$) and FT4 ($P<0.001$) and however show a significant statistical meaning for increase of TSH from 2.28±0.16 µu/ml to 4.54±0.01 µm/ml ($P<0.001$).

(2) As shown in Table 5, the L-T4 induced hyperthyroidism rats treated with PBT (25 mg/kg, P.O.) from Corydalis extracted chloroform B layer will remarkably decrease T3 ($P<0.05$), T4 ($P<0.05$), FT3 ($P<0.05$) and FT4 ($P<0.01$) in the blood in comparison with the control test, and show no significant statistical difference from the control group as regards the TSH concentration in the blood; PBT treatment (50 mg/kg, P.O.) also remarkably reduces the T3 ($P<0.05$), T4 ($P<0.05$), FT3 ($P<0.01$) and FT4 ($P<0.01$) but showing no significant difference for TSH value in comparison with the control test; THP treatment (5 mg/kg, I.P.) will greatly reduce T3 ($P<0.01$), T4 ($P<0.05$), FT3 ($P<0.01$) and FT4 ($P<0.01$) in comparison with the control group and show no remarkable influence on TSH concentration in blood; and however the PTU treatment (5 mg/kg, P.O.) may increase the TSH concentration from 0.99±0.11 to 3.98±0.51 µg/ml ($P<0.001$) to show significant statistical meaning, even PTU treatment may decrease the T3 ($P<0.001$), T4 ($P<0.001$), FT3 ($P<0.001$) and FT4 ($P<0.001$).

TABLE 5

| Treatment | TSH (µu/ml) | T3 (ng/dl) | T4 (µg/dl) | FT3 (ng/dl) | FT4 (ng/dl) |
|---|---|---|---|---|---|
| H.P. | 0.99 ± 0.11 | 72.76 ± 7.87 | 6.62 ± 0.53 | 4.04 ± 0.5 | 9.11 ± 0.87 |
| HP + PBT 25 mg/kg | 0.89 ± 0.10 | 49.9 ± 8.89* | 5.12 ± 1.10* | 1.79 ± 0.57* | 5.74 ± 0.85* |
| HP + PBT 50 mg/kg | 0.93 ± 0.10 | 50.95 ± 11.83* | 5.09 ± 1.2* | 1.53 ± 0.59** | 5.69 ± 0.95** |
| HP + THP 5 mg/kg | 0.77 ± 0.10 | 42.36 ± 4.25** | 4.91 ± 0.17* | 1.42 ± 0.62** | 5.27 ± 1.05** |
| HP + PTU 5 mg/kg | 3.98 ± 0.51*** | 30.25 ± 3.25*** | 1.95 ± 0.25*** | 2.01 ± 0.25*** | 3.24 ± 0.98*** |

Mean ± SE (n = 6)
HP: Hyperthroidism induced by L-T4 300 µg/kg s.c. for 12 days.
Significantly different from H.P. (*$P < 0.05$, $P < 0.01$, *$P < 0.001$).

From the above-mentioned experiments, both THP and PBT may markedly decrease the concentration of T3, T4, FT3 and FT4 in the hyperthyroidism rats and will not influence the TSH concentration in the blood. However, the dosage of THP is much smaller than the dose of PBT but the THP reveals its pharmacological effect not less than that of the PBT.

The effects of THP on thyroid, pituitary and suprarenal gland weight, on the thyroid function of normal rats and also the THP effects on the thyroid function, blood cholesterol and triglyceride level in L-T4 induced hyperthyroidism rats are discussed ahead in accordance with the present invention.

EXPERIMENT 4

Effect of dl-tetrahydropalmatine (THP) on thyroid function of normal rats

The method of experiment 1 is repeated by daily

TABLE 4

| Treatment | TSH (µu/ml) | T3 (µg/dl) | T4 (µg/dl) | FT3 (ng/dl) | FT4 (ng/dl) |
|---|---|---|---|---|---|
| Normal Group | 2.28 ± 0.16 | 54.09 ± 3.44 | 2.72 ± 0.20 | 1.21 ± 0.90 | 2.01 ± 0.23 |
| PBT 25 mg/kg | 1.89 ± 0.12 | 56.93 ± 3.12 | 2.25 ± 0.49 | 1.34 ± 0.05 | 1.69 ± 0.5 |
| PBT 50 mg/kg | 2.47 ± 0.37 | 58.75 ± 3.73 | 2.45 ± 0.22 | 1.20 ± 0.2 | 2.06 ± 0.2 |
| THP 50 mg/kg | 1.89 ± 0.13 | 49.05 ± 2.45 | 2.32 ± 0.25 | 1.18 ± 0.01 | 1.97 ± 0.14 |
| PTU 5 mg/kg | 4.54 ± 0.41*** | 31.77 ± 3.10*** | 0.92 ± 0.14*** | 0.37 ± 0.10*** | 0.35 ± 0.09*** |

Mean ± SE (n = 6)
Sifnificantly different from normal group (***$P < 0.001$).

treating dl-tetrahydropalmatine (THP) 2.5 mg/kg, 5.0 mg/kg and 10 mg/kg (I.P.) respectively for continuous 14 days. The results thereby obtained show no influence on the concentrations of T3, T4, FT3, FT4 and TSH, indicating that THP has no influence on thyroid function of normal rats.

Comparatively, PTU reduces the T3, T4, FT3 and FT4, but increases the TSH concentration to thereby expand thyroid follicle cells and cause colloidal loss, and is therefore inferior to the Corydalis invention.

TABLE 6

| Treatment | Dose (mg/kg) | TSH (μu/ml) | T3 (ng/dl) | T4 (μg/dl) | FT3 (ng/dl) | FT4 (ng/dl) |
|---|---|---|---|---|---|---|
| Normal Control group | saline | 2.3 ± 0.2 | 54.1 ± 3.4 | 2.7 ± 0.2 | 1.2 ± 0.1 | 2.0 ± 0.2 |
| THP[1] | 2.5 | 1.9 ± 0.1 | 56.8 ± 3.1 | 2.3 ± 0.5 | 1.3 ± 0.1 | 1.7 ± 0.5 |
| THP | 5.0 | 2.5 ± 0.4 | 58.8 ± 3.7 | 2.5 ± 0.2 | 1.2 ± 0.2 | 2.1 ± 0.2 | |
| THP | 10.0 | 1.9 ± 0.1 | 49.1 ± 2.5 | 2.3 ± 0.3 | 12. ± 0.1 | 1.9 ± 1.5 |
| PTU[2] | 5.0 | 4.5 ± 0.4*** | 31.8 ± 3.1*** | 0.9 ± 0.1*** | 0.4 ± 0.1*** | 0.4 ± 0.1*** |

Mean ± SE (n = 6)
[1]THP: dl-tetrahydropalmatine.
[2]PTU: propylthiouracil.
Significantly different from normal group (***$P < 0.001$).

EXPERIMENT 5

Effects of THP on rat thyroid function and on blood cholesterol and triglyceride in rats The method of experiment 3 is repeated by treating (I.P.) THP for continuous 10 days to know that THP increases the cholesterol by a much smaller amount than PTU and reduces the risk of arteriosclerosis due to the use of this invention. The THP of this invention may reduce the triglyceride of the hyperthyroidism rats to be superior to PTU.

Therefore, the THP of the present invention may treat hyperthyroidism by enhancing thyroid function.

TABLE 7

| Treatment | Dose (mg/kg) | Cholesterol (mg/dl) | Triglyceride (mg/dl) | T4 (μg/dl) |
|---|---|---|---|---|
| Normal Control Group | Saline | 66.1 ± 4.3 | 29.5 ± 2.3 | 2.2 ± 0.2 |
| HP Group (HP[1]) | | 43.2 ± 3.5 | 40.8 ± 4.5 | 4.7 ± 0.8 |
| HP + THP[2] | 2.5 | 57.5 ± 3.5* | 29.5 ± 3.5* | 3.3 ± 0.4** |
| HP + THP | 5 | 58.5 ± 3.4* | 31.1 ± 5.4* | 3.1 ± 0.5** |
| HP + THP | 10.0 | 56.5 ± 4.6* | 30.6 ± 5.1* | 3.2 ± 0.5** |
| HP + PTU[3] | 5.0 | 73.9 ± 3.2** | 35.6 ± 3.2 | 1.2 ± 0.2 |

Means ± SE (n = 6)
[1]Hyperthyroidism (HP): induced by L-T4 300 μg/kg. s.c. for 12 days.
[2]THP: dl-tetrahydropalmatine treatment for 10 days.
[3]PUT: propylthiouracil treatmentfor 10 days.
Significantly different from hyperthyroidism (*$P < 0.05$, $P < 0.01$, *$P < 0.001$).

EXPERIMENT 6

Effect of THP on rat thyroid, pituitary and suprarenal gland weight

The method of experiment 1 is repeated by treating (I.P.) THP for 14 days to know that there is no influence on the weight of thyroid, pituitary and suprarenal glands of the rats. However, the PTU treatment may have side effects such as an increase of thyroid weight, expansion of follicle cells and colloidal loss.

EXPERIMENT 7

ICR mice each having weight of 18–25 grams are quantitatively treated with Corydalis extracted chloroform B layer as per Litchifield and Wilcoxon method to measure LD$_{50}$ and 95% confidence limit after 72 hours treatment per os to obtain the results as shown in Table 9.

TABLE 9

| Drug | Route | LD50 (g/kg) | 95% confidence limit (g/kg) |
|---|---|---|---|
| Corydalis extracted Chloroform B layer | P.O. | 1.42 | 1.20–1.68 |

The THP of this invention may be treated either peroral or non-peroral. If it is treated per os, an effective constituent of THP is added with pharmaceutical acceptable additives such as carrier, formative agent or diluent to tablets, granules, powders, capsules for a patient's safe dosage.

The non-peroral treatment may take the form of, for example, subcutaneous, intramuscular or intravenous injections.

The treatment quality of THP depends upon the symptoms and ages of the patients. A daily dose of

TABLE 8

| Treatment | Dose (mg/kg) | Body weight (g) | Thyroid (mg/ 100 g body weight) | Pituitary (mg/100 g) | Suprarenal gland (mg/100 g) |
|---|---|---|---|---|---|
| Control Group | Saline | 246.0 ± 14 | 8.9 ± 1.0 | 18.9 ± 3.0 | 24.2 ± 4.4 |
| THP[1] | 2.5 | 272.0 ± 9 | 8.4 ± 1.5 | 18.1 ± 2.6 | 27.9 ± 2.7 |
| THP | 5.0 | 261.0 ± 15 | 8.5 ± 1.5 | 17.4 ± 2.8 | 26.2 ± 4.9 |
| THP | 10.0 | 257.0 ± 15 | 8.0 ± 1.5 | 17.9 ± 2.7 | 24.1 ± 3.6 |
| PTU[2] | 5.0 | 261.0 ± 10 | 26.8 ± 2.5** | 20.0 ± 2.4 | 27.1 ± 3.8 |

Mean ± SE (n = 6)
THP: dl-tetrahydropalmatine. treated for 14 days.
PTU: Propylthiouracil. for 14 days.
Significantly different from control group (**$P < 0.01$).

25–75 mg can be divided into several dosages, whereas a dose of 10–30 mg per day can be administered in a single injection. The injection may be applied once or several times a day for the dosage of 10–30 mg per day.

The examples for making tablets and injection are shown as follows:

EXAMPLE 1

| For tablet form, the composition per tablet is as follows: | |
|---|---|
| THP | 25 mg |
| Lactose | 25 mg |
| Starch | 140 mg |
| Magnesium stearate | 10 mg |
| Total | 200 mg |

The ingredients of the above prescription are ground and mixed for obtaining granules which are then dried, and processed as tablets.

EXAMPLE 2

THP 10 mg is dissolved in 0.1 ml 10% phosphoric acid and a sterilized injection water 1.9 ml is added in the mixed solution, of which 1N NaOH is added to adjust the pH value of the solution to 4.5 to thereby obtain an injection containing 10 mg THP in 2 ml injection liquid stored in each ampule.

Prescription: Each 2 ml ampule contains:

| THP | 10 mg |
|---|---|
| Sterilized injection water made up to a total volume | 2 ml. |

We claim:

1. A method for treating hyperthyroidism comprising perorally administering to a patient a pharmaceutical composition comprising dl-tetrahydropalmatine having a structural formula of:

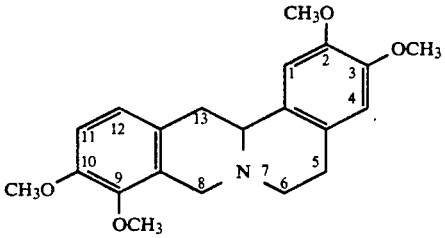

and a pharmaceutically acceptable carrier for said dl-tetrahydropalmatine, said pharmaceutical composition being administered in an amount sufficient to provide a daily dose of 25 to 75 mg of dl-tetrahydropalmatine to said patient.

2. A method according to claim 1, wherein said pharmaceutical composition is in the form of a tablet and comprises dl-tetrahydropalmatine, lactose, starch and magnesium stearate.

3. A method for treating hyperthyroidism comprising administering to a patient by injection a pharmaceutical composition comprising dl-tetrahydropalmatine having a structural formula of:

in an injectable aqueous medium, said pharmaceutical composition being administered in an amount sufficient to provide a daily dose of 10 to 30 mg of dl-tetrahydropalmatine to said patient.

* * * * *